United States Patent [19]

Sundrehagen

[11] Patent Number: 5,242,842

[45] Date of Patent: Sep. 7, 1993

[54] GLYCOSYLATED HAEMOGLOBIN ASSAY

[75] Inventor: Erling Sundrehagen, Oslo, Norway

[73] Assignee: Axis Research AS, Oslo, Norway

[21] Appl. No.: 613,505

[22] PCT Filed: May 11, 1990

[86] PCT No.: PCT/EP90/00820

§ 371 Date: Nov. 1, 1990

§ 102(e) Date: Nov. 1, 1990

[87] PCT Pub. No.: WO90/13818

PCT Pub. Date: Nov. 15, 1990

[30] Foreign Application Priority Data

May 11, 1989 [NO] Norway .................................. 891929

[51] Int. Cl.$^5$ ............................................. G01N 33/72
[52] U.S. Cl. ...................................... 436/536; 436/66;
436/161; 436/166; 436/175; 436/177; 436/815;
436/824; 436/539; 436/67
[58] Field of Search ........................ 422/52, 56, 57, 61,
422/82, 82.05, 82.08; 436/501, 512, 539, 536,
56, 63, 66, 67, 166, 169, 172, 178, 161, 175, 177,
815, 824

[56] References Cited

U.S. PATENT DOCUMENTS

| | | | |
|---|---|---|---|
| 4,268,270 | 5/1981 | Gabbay et al. | 436/57 X |
| 4,269,605 | 5/1981 | Dean et al. | 436/67 |
| 4,371,374 | 2/1983 | Cerami et al. | 422/57 X |
| 4,407,961 | 10/1983 | Sanders | 436/67 |
| 4,659,817 | 4/1987 | Gallop et al. | 436/544 X |
| 4,820,636 | 4/1989 | Hill et al. | 436/67 X |
| 4,861,728 | 8/1989 | Wagner | 436/531 X |
| 5,137,833 | 8/1992 | Russell | 436/94 |

OTHER PUBLICATIONS

Van Dam et al., Biotechnology and Applied Biochemistry 11, 492–502 (1989).

Primary Examiner—James C. Housel
Assistant Examiner—Jeffrey R. Snay
Attorney, Agent, or Firm—Bacon & Thomas

[57] ABSTRACT

A method of assessing glycosylated haemoglobin in a sample, wherein the method comprises the steps of (a) contacting the sample with signal-forming molecules comprising a conjugate of one or more dihydroxyboryl residues or salts thereof, linked to a signal-forming label; (b) separating by selective precipitation from a homogenous solution, glycosylated and non-glycosylated haemoglobin and any molecules bound thereto, from the reaction mixture of step (a) above; and (c) assessing signal-forming molecules selected from the group consisting of signal-forming molecules which have bound to the separated haemoglobin, and non-haemoglobin bound signal-forming molecules. Steps (a) and (b) may be performed simultaneously or sequentially. The sample may optionally be haemolyzed to liberate any cell bound haemoglobin. The invention also comprises an analytical test kit for use in accordance with the method of the invention. The new assay of the invention is particularly useful for the in vitro diagnosis and monitoring of diabetes mellitus.

16 Claims, 2 Drawing Sheets (1)   Haemoglobin (2)   Haemoglobin/Resos - aminophenyl boronic acid conjugate

GLYCOSYLATED HAEMOGLOBIN ASSAY

BACKGROUND OF THE INVENTION

The present invention relates to a ligand binding assay for specific assessment of glycosylated hemoglobin.

Proteins in solution in body fluids are continually subject to glycosylation processes. Glucose reacts with the proteins by non-enzymatic reactions to form glycoproteins, and in many cases the level of glycoprotein formation is proportional to the glucose concentration in the body fluid in question. For proteins not initially synthesized as glycoproteins, the fraction of a protein present in glycosylated form is therefore a function of
the life-time of the protein in the organism and
the glucose concentrations to which the protein has been exposed.

Unlike measurements of glucose concentrations in blood, plasma or urine, which only give information about the glucose concentration at the time of sampling, the amount of a protein present in glycosylated form gives an indication of the organism's control of glucose concentration during longer periods of time.

Erythrocytes (red blood cells) have a mean lifetime of approximately 120 days and contain large amounts of haemoglobin. The fraction of erythrocyte haemoglobin in glycosylated form is thus a good measure of the control of the disease in patients with diabetes mellitus, and is a function of the glucose concentrations in the blood of the patient in the weeks prior to the blood sampling.

In clinical practice numerous different methods have been used to measure the glycosylated haemoglobin fraction in order to quantitatively evaluate the long-term control of blood glucose in patients with diabetes mellitus. The main methods which are in clinical use are:

1. Separation of glycosylated and non glycosylated haemoglobins by means of ion-exchange chromatography. This was the first method proposed and still is the clinical method most commonly used. High costs and time-consuming manufacturing methods together with time-consuming performance of the separations are drawbacks of the method, and the results are influenced by small temperature variations.

2. Use of boronic acid derivatives to specifically isolate the glycosylated haemoglobin fraction. It has long been known that boronic acid moieties bind to carbohydrate moieties having cis-diol residues, (Boeseken J., Advances in carbohydrate chemistry 4, 189-210, 1949. Solms J. and Deuel H., Chimica 11, 311, 1957) and this property can be used as the basis for an affinity chromatographic seperation. Thus, for example, boronic acid residues have been chemically immobilized on solid phases such as agarose, for isolation of glycoproteins, carbohydrates and nucleotides (Hageman, J and Kuehn, G., Anal Biochem. 80: 547, 1977.). Columns of such material have also been used to quantify the glycosylated fraction of haemoglobin (Dean P. D. G. & al, UK patent application GB-A-2024829). Such columns are time-consuming and expensive to make and slow to run: Haemolysate must be passed through the column, the different fractions must be collected and the volumes of the fractions must be corrected, before the haemoglobin content of the different fractions can be measured and the fraction of haemoglobin in glycosylated form can be calculated.

3. Electrophoretic separation. Glycosylation of haemoglobin alters the electric charge of the protein, and this may be used to separate the glycosylated and non-glycosylated fractions electrophoretically, following which the different fractions may be quantitated for example by reflectometry. This method is also time-consuming and expensive.

In addition to the glycosylation of haemoglobin within erythrocytes, glycosylation of proteins in serum takes also place at an elevated rate in patients suffering from diabetes mellitus. However, since the different serum proteins have different half-lives in the body, and most of these half-lives are significantly shorter than that of haemoglobin, measurements of glycosylated serum proteins are only used for short to intermediate term retrospective monitoring of the regulation of the disease. Different colorimetric methods for quantitation of glycosylated serum proteins are widely used as an index of diabetic control (Johnsen, Metcalf & Baker, Clinical Chimica Acta 127 (1982) 87-95). However, the quantitation of glycosylated serum proteins has limited clinical value because of the short lifetime of most serum proteins, which is equally true for the glycosylated form. Moreover, from a technical point of view, quantitation of carbohydrates bound to serum proteins requires the collection and preparation of serum which is time-consuming and cumbersome to perform (vein puncture, coagulation for 2 hours, centrifigation and decantation) compared to determination of blood glucose in diabetic patients, which can be performed by microsampling of capillary blood only.

None of the prior art methods for quantitation of glycosylated hemoglobin has become established as an absolute standard method. For one thing, fractions isolated in the different known methods do not exactly correspond ("Measurement of Glycosylated Hemoglobins using affinity chromatography" Bouriotis et al, Diabetologia 21: 579-580, 1981). In ion exchange methods, the fraction named HbAlc is often called "glycosylated hemoglobin", however this fraction may also contain non-glycosylated hemoglobins, and several glycosylated hemoglobins are eluted in different fractions.

Affinity chromatography using immobilized boronic acid residues isolates haemoglobins glycosylated at different residues, including for example haemoglobin glycosylated at lysine residues, in addition to the more common fraction glycosylated at the amino terminal of the $\beta$-chain. However, non-glycosylated haemoglobins can also become unspecifically bound to the solid phase used in this method, and not all glycosylated haemoglobin may be bound if the glycosyl moieties are located within the molecule and are not available for binding to solid phases. The different methods for quantitation of glycosylated hemoglobins which are used therefore have different reference range values.

A further problem is that in several methods high levels of glucose will interfere with the quantitation of the glycosylated fraction.

In addition to the said glycosylated fraction of the haemoglobins where glucose is covalently bound to the haemoglobin, there is another glycosylated fraction where the glucose is more loosely bound. These glycosylated haemoglobins are often referred to as "labile" glycohaemoglobins, since their formation may be reversed by washing the erythrocytes or by incubating the erythrocytes in carbohydrate-free solution, or by exposing the glycosylated haemoglobin to pH 5 (Bisse, Berger & Fluckinger, Diabetes 31: 630-633, 1982). However, the geometrical structure of the boronic ester formed with glycosylated haemoglobin is predominantly obtained with the non-reversibly glycosylated forms, and not with the labile preglycosylated form.

As regards alternative forms of assay, immobilization of antibodies on solid phases is commonly used in immunoassay techniques and in immunopurification of proteins and cells. Antibodies may also be used in homogeneous immunoassays, i.e. where both antibodies and antigens are present in solution, and where the antibody/antigen reaction may be measured directly (e.g. by nephelometric or turbidimetric methods) or indirectly (by means of fluorescence or enzyme activation or inhibition). Numerous attempts have been made to use monoclonal and polyclonal antibodies specific for glycosylated haemoglobin, but with limited success. This is mainly due to the fact that most of the carbohydrate residues of glycosylated haemoglobin are present in chemical forms not readily accessible for binding to monoclonal antibodies. Thus, denaturation of the glycosylated haemoglobin is often necessary to achieve such binding, e.g. by adsorption to polystyrene surfaces (Engbaeck F. & al: Clinical Chemistry 35:93-97, 1989) or by chemical denaturation (Knowles 7 al: U.S. Pat. No. 4,658,022, 1987).

Burnett J. B. & al (Biochemical and Biophysical Research Communication, vol. 96, p. 157-162, 1980) have synthesized a fluorescent boronic acid molecule, N-(5-dimethylamino-1-naphthalene sulfonyl)-3-aminobenzene boronic acid, which was demonstrated to bind to cell membranes for fluorescent microscopy of cells.

Fluorescent and coloured diazo conjugates of boronic acids for quantification of total glycosylated proteins present in a sample were described by Schleicher in German patent application DE 3720736, published Jan. 5, 1989. The Schleicher method relies on one of the following three principles for measurement of total glycoprotein present in a sample:

1. A shift in the absorption maximum of the boronic acid conjugate when bound to glycosylated moities of glycoproteins present, or 2. a polarization change of fluorescence when the fluorescent boronic acid conjugates bind to glycosylated moities of the total glycoproteins present, or 3. measuring the amount of the coloured or fluorescent boronic acid conjugate bound to the total glycoprotein present after removal of excess unbound boronic acid conjugate, for example using activated charcoal.

None of the methods described by Schleicher (ibid) can however be used for the quantitation of a specific glycoprotein in a mixture of other glycoproteins, and especially not for the specific determination of glycosylated haemoglobin in haemolysate samples from patients. In addition, the reagents described by Schleicher have rather low absorption coeffecients and their absorption maxima lie close to those of haemoglobin, making it difficult or impossible to detect glycosylated haemoglobin even when it is present in pure form. Indeed Schleicher makes no mention of the use of his method for the analysis of glycosylated haemoglobin, but proposes instead the analysis of total serum glycosylated proteins and glycosylated albumin extracted from human serum.

Lectins reactive to glycoproteins have also been investigated, although so far no lectins specifically reactive to glycosylated hemoglobin and useful in the quantitation of glycosylated haemoglobins have been identified.

A need therefore exists for an improved method of assaying glycosylated haemoglobin which is specific, rapid, simple to use and readily adapted for use in clinical laboratories.

SUMMARY OF THE INVENTION

We have now found that by combining the separation of both glycosylated and non-glycosylated haemoglobin fractions from a sample with the specific carbohydrate-recognising property of boronic acid derivatives to detect only the glycosylated fraction, an efficient and specific assay may be achieved.

Viewed from one aspect the present invention therefore provides a method of assessing glycosylated haemoglobin in a sample, said method comprising the steps of (a) optionally haemolysing the sample to liberate any cell bound haemoglobin.

(b) contacting the said sample or haemoglobin recovered from said sample according to step (c) below with signal-forming molecules comprising a conjugate of one or more dihydroxyboryl residues or salts thereof, linked to a signal-forming label;

(c) separating glycosylated and non-glycosylated haemoglobin and any molecules bound thereto, from the sample or from the reaction mixture of step (b) above; and (d) assessing the said signal forming molecules which have bound to the separated haemoglobin, and/or any non-haemoglobin bound signal-forming molecules.

In addition to determining the level of glycosylated haemoglobin within a sample, in carrying out the method of the invention it may also be desirable to obtain an assessment of the level of glycosylated and non-glycosylated haemoglobin present and to calculate a ratio of glycosylated to total haemoglobin.

The haemoglobin separating step does not require the separation of the total amount of haemoglobin lycosylated and non-glycosylated) present in the sample. It is sufficient for only a proportion of both the glycosylated and non-glycosylated fractions to be separated as long as the method is appropriately calibrated. Such calibrations are routine in clinical laboratory assays.

As used herein the term "assessing" is intended to include both quantitation in the sense of obtaining an absolute value for the amount of glycosylated or total haemoglobin in a sample, and also obtaining an index, ratio, percentage or similar indication of the level of glycosylated haemoglobin for example relative to the total haemoglobin concentration of the sample.

It will be appreciated that the new method of the invention avoids the separation of the glycosylated from the non-glycosylated haemoglobin fraction, but relies instead on a separation of both glycosylated and unglycosylated haemoglobin from a sample. Consequently there is no need for the signal-forming boronic acid derivatives to be immobilised since they are not used as part of a separation system, and indeed it is preferred that they are not immobilised.

The method of the invention may be used to assess the amount of glycosylated haemoglobin in samples of blood, blood haemolysates or blood extracts, both from healthy individuals or from patients suffering from or suspected to suffer from diabetes mellitus. It is especially useful for the assessment of haemoglobin in blood or haemolysate or other mixtures comprising other glycosylated proteins and/or glycoproteins and/or carbohydrates in addition to glycosylated hemoglobin. The samples may be in dry, liquid or frozen form before analysis. Haemolysates for analysis by the method of the invention may be prepared for example using different kinds of reagents to haemolyse and expose the carbohydrate moieties of the glycosylated haemoglobins to the binding reactions. This treatment can be performed prior to or in combination with the use of the other reagents necessary for the performance of this method. Optionally to reduce interference the samples may be treated to reduce the levels of free glucose and/or labile glycohaemoglobins present, e.g. using glucose oxidase or a buffering solution with a pH below

DETAILED DESCRIPTION OF THE INVENTION

Figure 1:
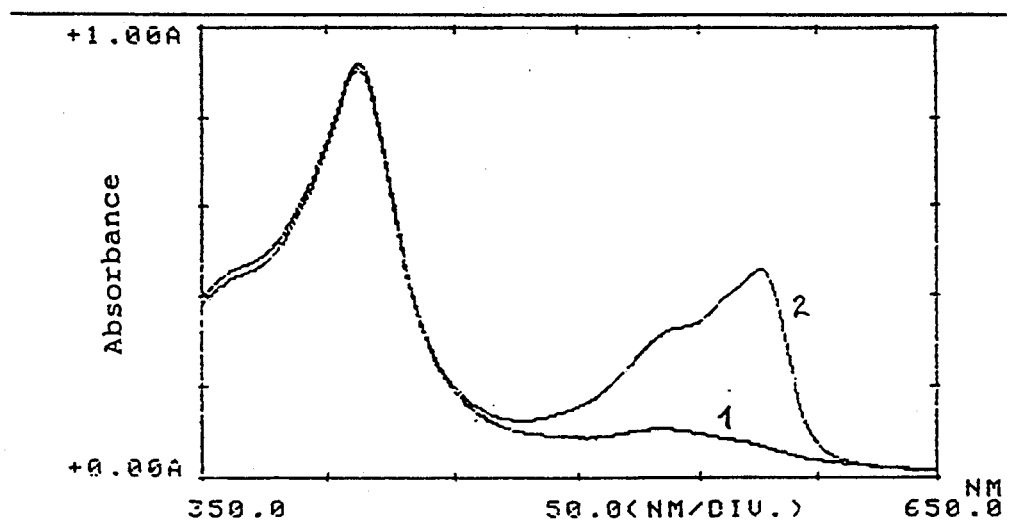
FIG. 1 shows the absorption spectrum of haemoglobin bound to a signal forming molecule in accordance with the invention.

In the method of the invention, the reaction of the signal-forming molecules or conjugates with the haemoglobins may take place either before or after the haemoglobin is separated from the sample. The order chosen depends on the chemical equipment or instruments to be used for the performance of the method and what is found more practical.

In one preferred embodiment of the invention the binding of the signalforming molecule and the isolation of haemoglobin takes place simultaneously in a homogeneous solution, from which the haemoglobin is precipitated and isolated by centrifugation or filtration. However, reaction and separation conditions must be chosen within the limitations of the glycosyl residue—boronic acid association constants, which are rather low ($10^3$–$10^5$ mol$^{-1}$.l).

From the strength of the signal obtained from the said signal forming molecules, the concentration of the signal forming molecules bound to or separated with the haemoglobins may be determined. As previously mentioned, a "absolute" standard for quantitation of glycosylated haemoglobin does not yet exist. However if desired a calibration or correlation of this new method to prior art methods may be obtained using standard haemoglobin solutions containing known concentrations of glycosylated haemoglobin as determined by prior art method(s).

The signal forming molecules and conjugates may conveniently comprise phenyl boronic acid residues, linked to a signal forming label either directly, by an amine or amide linkage, by a spacing moiety or by any kind of chemical linkage known in the art, which leaves the dihydroxyboryl residues free to react with the cis-diol residues of the glycosyl moieties of the haemoglobins. Dependent on which pKa value of the boronic acid residues is desired the phenyl ring may be further substituted, for example by nitro, formyl or alkoxy groups or by other substituents which influence the pKa-value, but do nôt sterically interfere with the binding to the cis-diol residues of the glycosylated haemoglobins.

The boronic acid residues used for the synthesis of the signal forming molecules of the present invention are conveniently synthesized from aminophenyl, for example m-aminophenyl, boronic-acid residues, and the linkage to the label or signal forming part of the said signal forming molecules or conjugates is typically achieved by means of diazonium ion formation, silanization, by use of coupling agents such as glutardialdehydes, carbodiimides, cyanogen halides, succinimides or any other coupling agents taught in the general chemical literature. The signal forming label is attached in a manner leaving the boronic acid residue free to react with the cis-diols of the glycosylated haemoglobin analyte and may be "activated" on beforehand in order to render it reactive with amine or other reactive moieties on the dihydroxyboryl residues e.g. dimethylaminoazo-benzene isothiocyanate and dimethylamino-naphthalene sulphonyl chloride. The signal forming molecules of the invention may also be further modified to increase water solubility.

The signal-forming dihydroxyboryl reagent for use in accordance with the invention is preferably present in a non-immobilized form, and comprises boronic acid residues linked, directly or indirectly, to chemical structures (labels) being able, directly or indirectly, to form signals, that can be used for chemical or physical quantitation purposes. The signal forming label may comprise enzyme(s), preferably enzymes not carrying carbohydrate cis-diol moieties or depleted with respect to fractions carrying cis-diol residues. Alternatively, the signal forming label may be partially or totally constituted by coloured or fluorescent moieties. A large range of coloured, fluorescent or pigmented compounds suitable for use as labels are known in the art and may be used. Suitable examples include anthraquinones, azodyes, azine dyes such as oxazines and thiazines, triazines, naturally occurring pigments such as porphyrins, phycobiliproteins, including phycoerythrins and phycocyanins, chlorophylls, and their analogues and derivatives, carotenoids, acrinidines,xanthenes, including fluoresceins and rhodamines, indigo-dyes, thioxanthenes, coumarines, polymethines, including di- and tri- arylmethines, and derivatives thereof and phtalocyanins and metal ptalocyanins, optionally linked by spacing moieties interposed between the signal forming label and the boronic acid residues, which are left free to react with the cis-diols of the glycoproteins to be analyzed.

Similarly, a wide range of radioactive compounds may be used as the signal forming label part of the reagent used in this invention, among them Iodine-125-labelled compounds. Such labelled compounds may conveniently be obtained by I-125-labelling of the carbon ring of the phenyl boronic acids or by conjugating aminophenylboronic acid to I-125-labelled reagents, e.g. the well known Bolton-Hunter reagent. A review of such radiolabelling techniques is given by Bolton in Biochem. J. 133: 529–539, 1973. In the performance of the method of this invention, rather high concentrations of reactants are necessary, thus in many embodiments of this invention the I-125-labelled conjugates can be mixed with non-radioactive boric acid or boronic acids with identical or different structure, to obtain a radioactivity of the assay reagents at an appropriate level.

Alternatively, the boronic acid residues may be conjugated to natural or synthetic compounds which can produce a chemiluminescent signal which may be assayed in known manner (Cormier, M. J. et al:, Chemiluminescence and Bioluminescence, Plenum Press, New York 1973). Suitable chemiluminescent compounds include luciferin, oxalic esters, 1,2-dioxethane, luminol or derivatives thereof, but are not limited to these. If appropriate hydrogen peroxide, enzymes e.g. luciferase, or other chemicals may be used to produce the chemiluminescent signal from the signal-producing molecules used.

Strongly-anionic signal forming conjugates are not preferred for use in the method of the invention, since they have a tendency to bind to serum proteins such as human serum albumin (HSA) which may be present in the sample. A particularly suitable example which may be used is the conjugate obtained by reaction of fluorescein isothiocyanate with aminophenyl boronic acid, resulting in a conjugate with a free carboxylic moiety. Other suitable conjugates include aminophenylboronic acid conjugated to fluorescein, e.g. by means of 1-ethyl-3(3-dimethylaminopropyl)-carbodimide (EDC), and fluorescein isothiocyanate having blocked carboxyl groups or where the carboxylic acid moiety has been removed conjugated to aminophenylboronic acid. Rhodamine B, conjugated e.g. by means of a carbodiimide, to an aminophenylboronic acid may also be used, however, this conjugate has a rather poor solubility in most solutions of interest for assay by the method of the invention. N-(resorufin)-4-carbonylpiperidine-4-carboxylicacid-N-hydroxysuccinimide-ester) (herein after abbreviated to resos) is a particularly preferred signal-forming molecule which the inventor has conjugated to aminophenyl boronic acid and which has been shown to exhibit excellent solubility properties and also low non-specific binding to proteins. This low protein binding may be due to the reduction in the number of anionic groups compared to conjugates such as FITC-aminophenyl boronic acid conjugate.

Boronic acid residues,

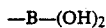

are often named dihydroxyboryl residues in their electrically neutral form, and form anions by the binding of hydroxyl ions

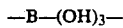

and may as such form salts. The reagents used in the method and provided by this invention may comprise residues with one or more of these forms of boronic acid, depending on the pH and electrolyte content of the reagent composition. It is in the anionic form that boronic acids bind to the cis-diol residues of glycosylated haemoglobins. However, the anionic strength of the boronic acid residues is sufficiently weak, so as not to give rise to problems in the binding to proteins such as HSA.

The use of high molecular weight signal-forming conjugates with boronic acids in the method of this invention is preferably avoided because of the limited accessability of the glycosylated moiety of most glycosylated haemoglobins; a substantial fraction of the glycosylated haemoglobin in blood is glycosylated at the N-terminal valine amino acid of the beta-chain, which is not readily available for water-soluble high molecular weight molecules, as described in the previously mentioned U.S. Pat. No. 4,658,022. This patent teaches the use of a very significant denaturation to expose the glycosylated residue to antibody binding reactions.

In accordance with one embodiment of the method of the invention, the total haemoglobin may be separated from the sample by means of immobilised binding proteins specific for haemoglobin such as antibodies or haptoglobin for example, coupled to surfaces such as filters, membranes, beads, gels, microtitre strips, tubes or plates, either by hydrophobic interaction or by chemical coupling either directly or by means of secondary antibodies. This is generally not preferred however since the association constants between boronic acid and the cis-diol residues of carbohydrates are in the range of $10^3$ to $10^5 \text{mol}^{-1}.\text{l}$. (Evans & al: Anal. Biochem, 95:383, 1979. Zittle C, Advan.Enzym. 12:493, 1951), and consequently since the effective concentration of binding protein is rather low when immobilised, the binding of the boronic acid to the cis-diol groups is also correspondingly reduced. High binding capacities are therefore required to compensate and these are difficult to achieve from a technical point of view. This also limits the use of solid phases with low binding capacity such as polystyrene surfaces. The solid phase binding capacity can, however, be increased by the use of gels, microbeads or other well known solid phases having a large surface area per unit volume, but such solid phases may be less practical for routine clinical use. When immobilised haemoglobin specific binding proteins are used to separate the haemoglobin, it is preferred that the signal-forming molecules are labelled other than with an alkaline-phosphatase enzyme label.

In more preferred embodiments of the invention the separation of the haemoglobins (and the signal forming molecules bound thereto) is achieved by selective precipitation of the total haemoglobins from homogeneous solutions e.g. by the use of appropriate precipitation reagents optionally combined with a chromatography, centrifugation or filtration system.

Thus the separation of haemoglobins may be effected by means of non-immobilised specific haemoglobin binding proteins such as specific monoclonal or polyclonal antibodies, haptoglobins from any species which bind human haemoglobins, or any other proteins which bind haemoglobin and form precipitate or otherwise remove the haemoglobin from solution. Thus monoclonal antibodies reactive to different epitopes or polyclonal antibodies can be used to form a precipitate with haemoglobin. Precipitation can also be obtained by means of secondary antibodies or by means of haptoglobins in combination with antibodies reactive to haptoglobin. Preferably antibodies without cis-diol moiteties, or depleted with respect to cis-diol containing moieties, or immunoreactive fragments thereof may be used.

However a drawback of this method is that since the association constant of the boronic acid containing signal-forming molecules and the glycosylated residues of glycosylated haemoglobins is only in the order of $10^3$ to $10^5 \text{mol}^{-1}.\text{l}$, rather high concentrations of reactants are necessary resulting in a rather high consumption of antibodies or haptoglobin per test.

In preferred embodiments of the invention specific haemoglobin precipitation from homogeneous solution is achieved by the use of metallic cations or organic solvents. This has the advantage that very high concentrations of haemoglobin can be used, the precipitates may easily be separated for example by centrifugation or filtration and the reagents are inexpensive and efficient.

One such embodiment makes use of the fact that haemoglobin is a very water soluble protein, and the inventor has obtained a specific or close to specific precipitation of haemoglobin from solution by the use of certain organic solvents, for example alcohols such as ethanol and/or butanol, ketones such as acetone, ethers, e.g. cyclic ethers such as dioxane and tetrahydrofuran, amide solvents such as dimethylformamide or diethylformamide, sulphoxide solvents such as dimethylsulphoxide, hydrocarbon solvents such as toluene, and halogenated hydrocarbon solvents such as chloroform. When precipitating a whole blood sample, diluted to give approximately 6.5 mg haemoglobin and 1.5 mg HSA/ml, by adding 50% butanol (v/v) in ethanol to a final concentration of 9% butanol (v/v), 94% of the haemoglobin was precipitated and only 1% of the HSA. Such precipitation was obtained without loss of the boronic acids residues bound to cis-diol moieties Specific precipitation of haemoglobin may also be achieved using metallic cations binding to and aggregating proteins. Suitable cations include zinc, copper, and less preferably nickel, cobalt and cadmium. This has the important advantage that any haemoglobin precipitated in this way may easily be re-dissolved by adding a solubilising complexing agent. Using zinc ions a substantially specific precipitation of haemoglobin from whole blood haemolysates can be obtained, which is an unexpected observation. By way of example, by using a zinc ion concentration of 2.5-4 mM in presence of 6.5 mg haemoglobin and 1.5 mg HSA/ml, a specific or close to specific haemoglobin precipitation is obtained. However a concentration above 4 mM zinc ions, substantial coprecipitation of HSA occured. This is illustrated by the results indicated below:

| Zn concentration (Mm) | % Hb precipitated | % HSA precipitated |
|---|---|---|
| 2.6 | 87 | 6 |
| 3.9 | 87 | 15 |
| 6.5 | 91 | 92 |

The ion concentration must however be carefully adjusted so as not to interfere with the signalforming boronic acid derivatives used. If desired, the precipitated haemoglobin may optionally be washed or filtered to remove excess cations before reaction with the signal-forming boronic acid conjugates. This reaction sequence is especially preferred when rather anionic signal forming boronic acid conjugates are used, since direct binding between excess zinc ions and the anionic conjugates may result in unwanted interference. In addition to zinc other metallic cations may be used, provided that they do not precipitate on their own in the buffering solution used for the precipitation reaction and that they have the same specific haemoglobin precipitation ability as zinc ions.

Due to the possibility of the metal ions participating in hydrolysis or other reactions with the other reagents in the test solution, precautions need to be taken to ensure that the metal cations remain soluble and available for the precipitation of the haemoglobin.

Some of the signal-boronic acid conjugates described in this specification contain groups which can donate a pair of electrons to the metal cations, and there by act as complexing agents. This ability to form ligand-metal complexes can be used to control the reactions, keeping the metal ion in solution, preventing the formation of complexes between the metal and the boronic acid signal forming derivatives, and ensuring availablility and high enough concentrations of the metal ion, to give the desired precipitation of haemoglobin in the test solution.

Since both ligand concentration and stability constants of different metal complexes need to be considered, appropriate buffer salts may be used to prevent the formation of insoluble metallic complexes (hereinafter referred to as Me-complexes).

Buffer salts forming weak monodentate Me-complexes are therefore preferred and an example of such a buffer is ammonium acetate in combination with zinc, forming soluble Zn(Ac) and Zn(HN$_4$) complexes.

By adding stronger complexing agents such as multidentate chelating ligands to the buffer, all the said rections can be controlled in test solution. The complexing agent is added in appropriate molar concentration to obtain the necessary molar ratios in the different complexes and to balance with other additives to ensure that all the reactions are performed optimally. Moreover, the complexing agent should be chosen with the particular metallic cation to be used in mind, to ensure that any potentially undersirable side effects such as too strong complexing of the metal ion are avoided.

The stability constant of the chelate-Me-complex has to be high enough to compete with other possible complexing agents in the test solution, for example the signal-boronic acid conjugate, but not so strong that the availability of the metal cation as precipitating agent is reduced or prevented.

Many chelating ligands may be used including ethylene-, propylene-, or butylene-diamine or analogues thereof, glycine, aspartate, nitriloacetate, histidine and picolinate. Several other natural or synthetic chelators such as carbohydrates, organic acids with more than one coordination group, aminoacids, peptides, phenolics and such like, may also be used but some of these are not preferred due to their ability to form complexes with boronic acid, i.e. salicylates, oxalates, carbohydrates such as sorbitol and tartrate, thereby competing with glycosylated haemoglobin for the binding to the signal-boronic acid conjugate.

Multidentate chelating ligands such as EDTA (ethylendiaminetetraaceticacid), CDTA (trans-1,2-diaminocyclohexane-N,N,N',N'-tetraaceticacid), EGTA (ethyleneglycol-o-o'-bis(2-amino-ethyl)-N,N,N',N'-tetraaceticacid), DTPA (dimethylene-triaminepentaaceticacid) etc. may also be used but in certain situations may be less preferred due to their very strong complexing ability with metal ions resulting in highly reduced precipitation of haemoglobin. Ammonium acetate buffer containing zinc ions and glycine is an example of a preferred combination.

Different complexing agents may be preferred in different embodiments of this invention. Complexing agents such as EDTA and DTPA are conveniently used, but their concentration must be carefully adjusted when combined with matallic cations used for precipitation of haemoglobin. Citric acid and oxalic acid are less preferred due to interaction with boronic acid residues Heparin and fluoride ions are other examples which may be used.

Precipitates obtained by precipitation from homogenous solutions, such as by the said use of organic solvents or metallic cations, can be totally or partially separated by means of centrifugation or filtration or by other techniques well known in the art.

Filter membranes or TLC-systems can also be used for the separation of the haemoglobin optionally with antibodies or immunoreactive fragments thereof, or haptoglobins immobilized thereon to bind the haemoglobin, such as in a dipstick or multilayer film format.

Separation of the haemoglobin by means of centrifugation followed by separation of the precipitate from the supernatant is one of the preferred methods. Alternatively filtration may conveniently be used, and this may be carried out either vertically to the filter surface through the filter, or tangentially or radially within the filter in a one-dimensional or two-dimensional separation method.

Thin layer chromatography methods can also be used. for example by application of the sample to a suitable chromatography medium, e.g. a test strip or gel, and application of reagents and washing solutions, for example directly to the site of application of the sample or by elution.

In further embodiments, the haemoglobin may be precipitated from solution directly onto or into a filter or other solid phase chromatography medium, in which case the precipitate may be deposited on or into the solid phase subsequent to or simultaneously with the formation of the precipitate. The reagents may be applied to a porous solid phase medium prior to, simultaneously with or after the precipitation step. Thus for example, reagents such as precipitating agents, the signal forming boronic acid reagents, haemolysing agents, complexing agents or other reagents; in any preferred combination, may be carried in or on the solid phase medium preferably in a dry form. Such reagent-carrying solid phase chromatography media form further aspects of the invention. The solid phase media may optionally be washed or an eluant solution may be eluted through the precipitation area.

To haemolyze the erythrocytes in a whole blood sample and to ensure a good chemical contact between the glycosylated haemoglobins and the signalforming boronic acid conjugates, a number of reagents and methods are generally known in the art and may be used, including hypotonic haemolysis, the use of detergents such as non-ionic polyethylene glycol ester or polyoxyethylene sorbitol ester derivatives e.g. "Triton" and "Tween", cholates, sodium dodecylsulphates, guanidine, heating, sonication, or any combinations thereto.

The signalforming boronic acid conjugates may be contacted with or mixed with the blood haemolysate samples or with haemoglobins isolated from such samples, in an assay buffer solution, subsequently to or simultaneously with the haemolysis treatment step.

A number of assay-buffers can be used, among them phosphate-buffers and other buffer solutions capable of maintaining the pH of the reaction mixture at a suitable pH. The preferred pH range of the assay is 7.5 10.0, but the desired pH is dependant upon the additives, buffer salts used and the pKa value of the boronic acid derivative used. There is some evidence that buffers containing amine may serve to strengthen the dihydroxyboryl-cisdiol interaction, or to lower the apparent pka value of the borate. Due to this fact buffers such as serine, glycine, Hepes (4-(2-hydroxyethyl)-1-piperazine-ethanesulphonic acid), ammonium acetate, morpholine and taurine are preferred. To further promote the interaction between dihydroxyboryl and cis-diol residues, additives such as divalent cations, detergents and chaotrophic agents may be used to reduce charge repulsions, solubilize target molecules, limit hydrophobic interactions and increase the accessability of the diols in glycosylated haemoglobin. However, certain buffers, like Tris and ethanolamines, should be avoided due to the fact that these buffer compounds can complex borate and block diols from binding. Certain buffer/additive combinations, like phosphate-zinc, are also unfavourable because of the possible formation of insoluble compounds like $Zn_3(PO_4)_2$.

The method of this invention may be performed within the temperature range of 4°–37° C. without significant differences in the results obtained.

The method of the invention involves the assessment or quantitation of the said signal-forming molecules (i.e. signal-reading the step) and optionally also of the total haemoglobin present in both glycosylated and non-glycosylated form. Depending on which embodiment of the method of this invention is used, the signal may be read from the haemoglobin bound signal forming molecules or from the non-haemoglobin bound signal-forming molecules remaining. Most practical is the assessment of the signal-forming molecules bound to the haemoglobins which have been previously isolated.

The assessment of the signal forming molecules bound to or separated with the haemoglobin is achieved by means of conventional chemical equipment commonly used for measuring enzymatic acitivity, fluorescence, radioactive radiation or optical density (absorbance), depending on the chemical nature of the signal forming label. Colour or fluorescence on a solid phase surface can readily be measured by means of reflectometry, which is in general use in clinical chemistry. On a dipstick or filter format or other practical solid phase format haemoglobins and/or fluorescent or coloured signalforming conjugates may be assessed directly on the surface. Alternatively, the precipitated or immobilized haemoglobin and/or the signalforming boronic acid conjugates may be redissolved and measured in solution.

Similarly, signal-forming boronic acid conjugates having an enzymatic acitivity may be assessed in immobilized or dissolved or redissolved form by means of enzymometric technology well known in the art. So also with radioactive boronic acid conjugates, which may be estimated using well known radiometric methods.

The concentration of both glycosylated and non-glycosylated haemoglobin separated may be determined by means of absorption at the relevant wavelengths in the reaction mixture prior to or after the separation step or alternatively the content of haemoglobin in the separated fraction may be measured. The latter is obtained by redissolving the haemoglobin followed by absorbance measurements, or by reflectometry of the isolated fractions, on a solid phase if necessary. If fluorescent signalforming molecules are to be quantitated in the presence of haemoglobin, excitation and emission wavelengths outside the absorption wavelengths of haemoglobin is preferred. Similarly, if a coloured signalforming molecule is used, an absorption wavelength outside that of haemoglobin is preferred as indicated in FIG. 1 with the absorption spectrum of haemoglobin (1) and a mixture of RESOS-aminophenyl boronic acid conjugate and haemoglobin (2). However, a partial interference from haemoglobin can be accepted and be corrected by calculations based on measurements at more than one wavelength.

In one embodiment of this invention, the haemoglobin and the bound signal-forming boronic acid conjugates are isolated on microbeads and/or a filter or other solid phase, followed by reflectometric quantitation of the haemoglobin and the signalforming boronic acid conjugates, either by light absorption measurements, or by measurements of fluorescence.

In further embodiments of this invention samples or aliquots of haemolysate depleted with respect to several or most or all other proteins reactive to boronic acid residues or salts thereof are used. e.g. erythrocytes can be washed before haemolysis in order to remove plasma proteins before the analysis of glycosylated haemoglobins in the samples. Alternatively haemolysate of whole blood can be exposed to an ion exchange solid phase separator to remove all proteins with isoelectric points below and/or above haemoglobin. This purification can optionally be a part of the apparatus or kit for the performance of the method of this invention.

In a special embodiment of this invention, the amount of the signal forming molecule or conjugate which is bound to haemoglobin in the presence and absence of a competing compound is measured. The competing compound can be any cis-diol containing molecule, e.g. sorbitol or mannitol, or boronic acid containing molecules with no signal forming activity.

In another special embodiment of this invention, the amount of signal forming molecules present, either in the reaction mixture and/or in the separated fraction before and subsequent to the separation of haemoglobin, is measured making it possible to calculate the fraction of the signal forming molecules removed by binding to the haemoglobin.

Since this invention relies on a rather low binding strength (association constant of $10^3$ to $10^5$ mol$^{-1}$.l between the cis-diol moieties and the boronic acid residues), a direct stoichiometric binding between glycosylated haemoglobin and the signalforming boronic acid conjugates does not take place. Furthermore, this invention provides a method where all the glycosyl moieties of the haemoglobin are readily accessed by the binding reactions, thus higher ratios of bound boronic acid conjugates: haemoglobin are obtained than the fraction glycosylated haemoglobin to total haemoglobin usually obtained by the prior art methods.

To a minor extent, free carbohydrates in blood may compete for the boronic acid residues. These effects are diminished by the use of an excess of the signal forming boronic acid conjugates. A twenty times molar excess is convenient, but higher and lower ratios can also be used, depending on which embodiment of this invention is used. Of course there will be a background signal depending on the efficiency of the separation techniques used. If a very efficient separation system is used, a higher excess can be used. If very high reactant concentrations cannot be used, the concentration of glycosylated haemoglobins should be calculated from the measurements by the used of standards having known concentrations of glycosylated haemoglobins and/or exact knowledge of the association constants. The use of such standards is very common in clinical laboratory medicine.

This invention also provides a reagent composition for the performance of the described method, said reagent comprising molecules comprising one or more boronic acid residues free to react with the glycosylated residues of glycosylated haemoglobins, linked to signal-forming labels, which may have enzymatic activity or be coloured, fluorescent, chemiluminescent or radioactive, as described above. Especially preferred are compositions having weakly anionic signal forming residues.

In a further aspect the invention also provides an analytical test kit for the performance of the method of the invention comprising:

(a) a reagent comprising a signal-forming molecule comprising a conjugate of one or more dihydroxyboryl residues or salts thereof, linked to a signal-forming label;

(b) means for the separation of haemoglobin from a sample;

optionally in combination with buffer salts or solutions.

The following examples and preparations are provided only by way of non-limiting illustration of the invention:

EXAMPLES

Preparations

Preparatory Example 1

1. N-(Resorufin)-4-Carbonylpiperidine-4-Carboxycyclicacid-N-Hydroxysuccinimideester (RESOS) Conjugate with Aminophenyl Boronic Acid Solution A: 2 mg RESOS was dissolved in 0.5 ml dimethylsulphoxide.

Solution B: The hemisulphate salt of m-aminophenyl boronic acid was dissolved 15 mg/ml in 0.1M sodium carbonate buffer, pH 8.0. pH was adjusted to 8.0.

Figure 2:
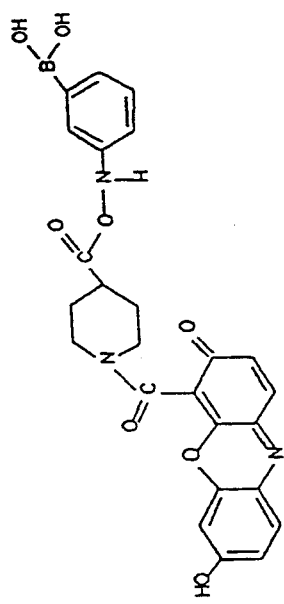
FIG. 2 is a chemical structure of one signal forming molecule in accordance with the invention.

0.5 ml solution A was added to 2 ml of solution B. The mixture was incubated at room temperature for 12 hours. Purification was performed by HPLC. The structure of conjugate is illustrated in FIG. 2.

Preparatory Example 2

2. Fluorescein Isothiocyanate (FITC) Conjugate with Aminophenyl Boronic Acid

Solution A: 3.9 ml mg of FITC was dissolved in 1 ml dimethylsulphoxide.

Solution B: The hemisulphate salt of m-aminophenyl boronic acid was dissolved 1.86 mg/ml in 0.2M carbonate buffer, pH 9.5

Figure 3:
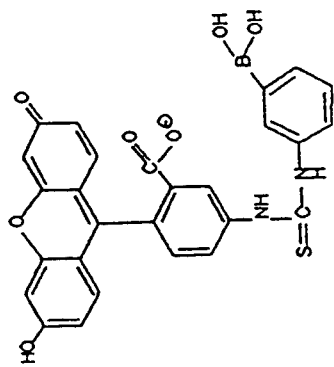
FIG. 3 is a chemical structure of another signal forming molecule in accordance with the invention.

1 ml solution A was added slowly to 10 ml solution B with constant stirring. The mixture was allowed to react for a minimum of 2 hours at room temperature, and the FITC-aminophenyl boronic acid conjugate was purified by HPLC. The structure of the conjugate is illustrated in FIG. 3.

Preparatory Example 3

3. Iodine-125-Labelled Boronic Acid Conjugate

A: Aminophenylboronic acid (APBA) 10 mg/ml in 50 mM Na-phosphate, pH 7.5 was reacted with Bolton-Hunter (BH) reagent 14.2 mg/ml in DMSO. BH was slowly added to the APBA up to an equal volume part. The solution was incubated for 1 hour at room temperature.

B: The reaction product was separated on a reversed phase column with a gradient of methanol in water with 0.1% trifluoroacetic acid (TFA).

C: The isolated BH-APBA reaction product was labelled with $^{125}$I-NaI by the chloramine-T method. 0.5 ml of BH-APBA fraction was added to 0.1 ml 0.25M Na-phosphate pH 7.5 and the pH was adjusted to 7.5. 10 μl $^{125}$I-NaI, 100 μCi was added in addition to freshly prepared 0.3 ml chloramin-T (10 mg/ml) in 0.25M Na-phosphate pH 7.5, and the mixture was incubated for 1 min.

D: The reaction was stopped by the addition of 0.3 ml Na-bisulfite (24 mg/ml) in 0.25M Na-phosphate pH 7.5.

E: Labelled BH-APBA was isolated by reversed phase chromatography by methanol gradient in water with 0.1% TFA.

Preparatory Example 4

4. Boronic Acid Conjugate with Alkaline Phosphatase

- 10 mg alkaline phosphatase, depleted with respect to boronic acid reactive enzyme molecules by passing through a column of agarose with immobilized phenyl boronic acid residues, is mixed with 30 times molar excess of bis-(sulfosuccinimidyl) suberate in carbonate buffer pH=8.5 and is left to react for 120 minutes at room temperature, followed by the addition of 100 times molar excess of monoethanolamine. 4 hours thereafter, the enzyme conjugates are purified by gel chromatography.

Examples Demonstrating Near Specific Precipitation of Haemoglobin from Whole Blood Haemolystates Metallic-cations:

Solution A: Whole blood haemolysate diluted in 50mM Ammonium acetate pH 8.0 to a final concentration of 6.4 mg heamoglobin/ml.

Solution B: Cu(SO$_4$) dissolved in water to a concentration of 10 mM Cu$^{2+}$

Solution C: Zn(Cl)$_2$ dissolved in water to a concentration of 10 mM Cu$^{2+}$

Preparatory Example 5

40 μl solution B was added to 200 μl solution A. The mixture was incubated at room temperature for 5 minutes and the haemoglobin precipitate separated by centrifugation.

Preparatory Example 6

40 μl solution C was added to 200 μl solution A. The mixture was incubated at room temperature for 5 minutes and the haemoglobin precipitate separated by centrifugation.

Examples of the Performance of the Method

Example 1

In all the following examplifications of the method, the method has been compared with the classical ion exchange HPLC method according to Jeppson, J. O. & al.: Clinical Chemistry 32/10, 1867–1872, 1988 (hereinafter abbreviated to "ion exchange" method).

A sample of whole blood was haemolysed and diluted in a haemolysing assay-buffer, 100 mM Hepes with 0.05% Triton X-100, pH 9.0, to approximately 8 mg haemoglobin/ml. A mixture of 50% (v/v) butanol in ethanol and FITC-aminophenyl boronic acid conjugate described above, was added to give a final butanol concentration of 9% (v/v), and a conjugate concentration of 1.6×10$^{-4}$M. A precipitate was formed, and the precipitate was separated from the supernatant by centrifugation. The precipitate was redissolved in 0.05M hydrochloric acid with 5% dimethyl sulphoxide and the concentration of haemoglobin was measured by absorption spectroscopy, and concentration of FITC-aminophenyl boronic acid conjugate was detected by fluorescence measurements. The concentration of haemoglobin and FITC-aminophenyl boronic acid conjugate was calculated by interpolation on calibration curves obtained by the use of standard solutions of known concentrations of haemoglobin and glycosylated haemoglobin, and the percentage of glycosylated haemoglobin to total haemoglobins was calculated.

The following illustrates the results obtained by performing the method as described.

| % glycosylated haemoglobin (ion exchange method) | molar ratio conjugate/haemoglobin |
| --- | --- |
| 4.8 | 0.284 |
| 7.8 | 0.344 |
| 11.7 | 0.431 |

Example 2

A sample of whole blood was haemolysed and diluted in a haemolysing assay-buffer to approximately 8 mg haemoglobin/ml and the FITC-aminophenyl boronic acid conjugate was added to a final concentration of 2×10$^{-4}$M. The sample was incubated for 30 minutes and 50% (v/v) butanol in ethanol was added to give a final concentration of 9% butanol (v/v). A precipitate was formed and was removed from the supernatant by centrifugation. The precipitate was dissolved in 0.05M hydrochloric acid with 5% dimethylsulphoxide, and the concentrations of haemoglobin and conjugate were measured as described in Example 5.

To verify the specificity of the FITC-aminophenyl boronic acid conjugate, the method was performed as described in Example 2, but a competing concentration, 0.1M, of sorbitol was added. This results in low, nonspecific binding of the conjugate to haemoglobin, and the results showed no difference between samples with high and low content of glycosylated haemoglobin, as illustrated below:

Results obtained without addition of sorbitol:

| % glycosylated haemoglobin (ion exchange method) | molar ratio conjugate/haemoglobin |
| --- | --- |
| 4.4 | 0.259 |
| 7.1 | 0.340 |
| 11.4 | 0.473 |

Results obtained with addition of sorbitol:

| % glycosylated haemoglobin (ion exchange method) | molar ratio conjugate/haemoglobin |
| --- | --- |
| 4.4 | 0.078 |
| 7.1 | 0.066 |
| 11.4 | 0.083 |

Example 3

The method was performed as described in Example 1, but instead of separating the precipitate by centrifugation, the precipitated sample was separated by filtration. A sample of whole blood was haemolysed and diluted in a haemolysing assay-buffer, 100 mM Hepes, 0.05% Triton X-100, ph 9.0, to approximately 8 mg haemoglobin/ml. A mixture of 50% (v/v) butanol in ethanol and FITC-aminophenyl boronic acid conjugate was added to give a final butanol concentration of 9%

(v/v) and a FITC-aminophenyl boronic acid conjugate concentration of $1.6 \times 10^{-4}$M. A precipitate was formed, and the precipitate was isolated by filtration followed by quantifications of the haemoglobin and the FITC-aminophenyl boronic acid conjugate isolated.

| % glycosylated haemoglobin (ion exchange method) | molar ratio conjugate/haemoglobin |
| --- | --- |
| 5.2 | 0.160 |
| 11.7 | 0.226 |

Example 4

A sample of whole blood was haemolyzed and diluted in haemolyzing assay-buffer, 100 mM Hepes with 0.05% Triton X- 100, ph 9.0, to approximately 8 mg haemoglobin/ml. A mixture of 50% (v/v) butanol in ethanol and RESOS-aminophenyl boronic acid conjugate described above, was added to give a final butanol concentration of 9% (v/v), and a conjugate concentration of $1.6 \times 10^{-4}$M. A precipitate was formed, and the precipitate was separated from the supernatant by centrifugation. The precipitate was redissolved in 0.05M hydrochloric acid with 5% dimethyl sulphoxide and the concentrations of haemoglobin and RESOS-aminophenyl boronic acid conjugate was measured by absorption measurements. The concentrations of haemoglobin and RESOS-aminophenyl boronic acid conjugate were calculated by interpolation on calibration curves obtained by the use of standard solutions of known concentrations of haemoglobin and glycosylated haemoglobin, and percentage glycosylated haemoglobin was calculated.

The following results have been obtained when performing the method as described.

| % glycosylated haemoglobin (ion exchange method) | molar ratio conjugate haemoglobin |
| --- | --- |
| 4.9 | 0.212 |
| 11.2 | 0.294 |

Example 5

The method was performed as described in Example 4, but instead of separating the precipitate by centrifugation, the precipitate was isolated by filtration. A sample of whole blood was haemolyzed and diluted in a haemolysing assay-buffer, 100 mM Hepes, 0.05% Triton X-100, pH 9.0, to approximately 8 mg haemoglobin/ml. A mixture of 50% (v/v) butanol in ethanol and RESOS-aminophenyl boronic acid was added to give a final concentration of 9% (v/v) butanol and a RESOS-aminophenyl boronic acid conjugate concentration of $1.6 \times 10^{-4}$M. A precipitate was formed and was isolated by filtration followed by quantitation of the haemoglobin and the RESOS-aminophenyl boronic acid conjugate isolated.

The following results have been obtained:

| % glycosylated haemoglobin (ion exchange method) | molar ratio conjugate/haemoglobin |
| --- | --- |
| 4.9 | 0.195 |
| 13.0 | 0.367 |

Example 6

A sample of whole blood was haemolysed and diluted in a haemolysing assay-buffer, 0.25M ammonium acetate with 0.05% Triton X-100, pH 9.0, to approximately 8 mg haemoglobin/ml. RESOS-aminophenyl boronic acid conjugate, $1.6 \times 10^{-4}$M, in a solution of 30 mM $ZnCl_2$ and 50 mM glycine was added to the haemolysed haemoglobin solution, and a precipitate was formed. The precipitate was removed from the supernatant by centrifugation followed by redissolving of the precipitate in 0.25M ammonium acetate buffer containing 30 mM EDTA, pH 9.0. The concentrations of haemoglobin and RESOS-aminophenyl boronic acid conjugate were assessed by absorption spectroscopy.

The results were as follows:

| % glycosylated haemoglobin (ion exchange method) | molar ratio conjugate/haemoglobin |
| --- | --- |
| 4.9 | 0.384 |
| 13.0 | 0.449 |

Example 7

The method was performed as described in Example 6, but the precipitated haemoglobin was separated by filtration followed by quantitation of the haemoglobin and the RESOS-aminophenyl a boronic acid conjugate.

Example 8

Haemolysated blood in Hepes buffer was added to iodine-125-labelled Boronic acid conjugate (see above). The haemoglobin concentration was 8 mq/ml.

After 30 min incubation, 22 µl of ethanol:butanol (1:1) was added and precipitated haemoglobin was separated by centrifugation.

The precipitate was dissolved by HCl/DMSO/water addition and haemoglobin content and radioactivity were measured.

A significant correlation between the radioactivity/haemoglobin ratio and glycosylated haemoglobin content was found.

Example 9

A sample of whole blood was heamolysed and diluted in a haemolysing assay-buffer, 100 mM Hepes with 0.05% Triton X-100, pH 9.0, to approximately 8 mg haemoglobin/ml. The RESOS-aminophenyl boronic acid conjugate was added to a final concentration of $2 \times 10^{-4}$M, $CuSO_4$ was added to a final concentration of 2 mM and a precipitate was formed. The precipitate was removed from the supernatant by centrifugation. The precipitate was redissolved in 0.05M hydrochloric acid with 5% dimethylsulphoxide, and the concentration of the haemoglobin and the RESOS-aminophenyl bornonic acid conjugate were measured as described in Example 1.

The results were as follows:

| % glycosylated haemoglobin (ion exchange method) | molar ratio conjugate/haemoglobin |
| --- | --- |
| 4.6 | 0.524 |
| 12.0 | 0.617 |

Example 10

A sample of whole blood was haemolysed and diluted in a haemolysing assay-buffer, 0.25M ammonium acetate with 0.05% Triton X- 100, to approximately 8 mg haemoglobin/ml. The FITC-aminophenyl boronic acid conjugate was added to give a concentration of $2 \times 10^{-4}$M. Isopropanol was added to give a final content of 33% (v/v), and a precipitate was formed. The precipitate was separated from the supernatant by centrifugation. The precipitate was redissolved in 0.05M hydrochloric acid containing 5% dimethylsulphoxide, and the concentration of the haemoglobin and the FITC-aminophenyl boronic acid conjugate were measured as described in Example 1.

The results were as follows:

| % glycosylated haemoglobin (ion exchange method) | molar ratio conjugate/haemoglobin |
| --- | --- |
| 4.8 | 0.260 |
| 12.5 | 0.398 |

Example 11

The method was performed as described in Example 10, but a precipitate was formed by addition of tetrahydrofuran to a final content of 50% (v/v).

The results were as follows:

| % glycosylated haemoglobin (ion exchange method) | molar ratio conjugate/haemoglobin |
| --- | --- |
| 4.8 | 0.255 |
| 12.5 | 0.429 |

Example 12

The method was performed as described in Example 10, but a precipitate was formed by addition of N,N-dimethylformamide to a final content of 15% (V/V).

The results were as follows:

| % glycosylated haemoglobin (ion exchange method) | molar ratio conjugate/haemoglobin |
| --- | --- |
| 4.8 | 0.197 |
| 12.5 | 0.211 |

I claim:

1. A method of assessing glycosylated haemoglobin in a sample containing both glycosylated and non-glycosylated haemoglobin in solution, said method comprising the steps of:
   (a) contacting the sample solution with signal-forming molecules comprising a conjugate of one or more dihydroxyboryl residues or salts thereof, linked to a signal-forming label, to form a reaction mixture containing glycosylated haemoglobin having said signal-forming molecule bound thereto;
   (b) precipitating from said reaction mixture by means of a non-immobilized precipitating agent glycosylated haemoglobin having said signal-forming molecule bound thereto, glycosylated haemoglobin and non-glycosylated haemoglobin;
   (c) separating said precipitate from said reaction mixture; and
   (d) assessing said signal-forming molecules which are bound to the separated haemoglobin, and assessing the separated glycosylated and non-glycosylated haemoglobin.

2. A method as claimed in claim 1 wherein the precipitate (e) is separated by centrifugation.

3. A method as claimed in claim 1, wherein the precipitate (c) is separated by means of a chromatography or filtration medium.

4. A method as claimed in claim 1, wherein haemolysis of whole blood by a method selected from the group consisting of hypotonic lysis, addition of detergents or guanidine, heating, sonication and any combination thereof forms the glycosylated and non-glycosylated haemoglobin in solution.

5. A method as claimed in claim 1 said precipitating agent has been depleted with respect to molecules reactive with dihydroxyboryl residues.

6. A method as claimed in claim 1, wherein whole blood is haemolyzed to form the solution containing glycosylated and non-glycosylated haemoglobin.

7. A method as claimed in claim 1 wherein said non-immobilized precipitating agent is selected from the group consisting of zinc ions, copper ions, other specific haemoglobin precipitating metallic cations and mixtures thereof.

8. A method as claimed in claim 7 further comprising adding a metal-complexing agent.

9. A method as claimed in claim 1 wherein said non-immobilized precipitating agent is an organic solvent, or a mixture of organic solvents, in a concentration which is able to substantially specifically precipitate the haemoglobin.

10. A method as claimed in claim 9 wherein said precipitating agent is a solvent which is selected from the group consisting of water miscible alcohols, ketones, ethers, amide solvents, sulfoxide solvents, hydrocarbon solvents, halogenated solvents and mixtures thereof.

11. A method as claimed in claim 1 wherein the signal-forming molecules exhibit a property selected from the group consisting of chemiluminescence, fluorescence, color, radioactivity and enzymic activity.

12. A method as claimed in claim 11 wherein said signal-forming molecules comprise a label selected from the group consisting of anthraquinones, azodyes, oxazines, thiazines, triazines, porphyrins, phycobiliproteins, chlorophylls and derivatives and analogues thereof, carotenoids, acrinidines, xanthenes, indigo dyes, thioxanthenes, coumarines, polymethines and derivatives thereof, phtalocyanins and metal phtalocyanins.

13. A method as claimed in claim 11 wherein said signal-forming molecules are labelled with N-(Resorufin-4-carbonyl)piperidine-4-carboxylic acid-N-hydroxysuccinimide ester (RESOS).

14. A method as claimed in claim 1, wherein the haemoglobin is precipitated by the addition of haemoglobin-specific binding proteins.

15. A method as claimed in claim 14 wherein said precipitating agent is selected form the group consisting of anti-haemoglobin antibodies, haptoglobins and fragments thereof.

16. A method as claimed in claim 15 wherein the haemoglobin is precipitated in the presence of a compound selected from the group consisting of secondary antibodies, secondary anti-haptoglobin antibodies and fragments thereof.

* * * * *